United States Patent
Lam

(10) Patent No.: US 10,293,061 B2
(45) Date of Patent: May 21, 2019

(54) TWO-ENDOSCOPE TECHNIQUE OF ENDOSCOPIC MUCOSAL RESECTION AND KIT WITH A SET OF ENDOSCOPES FOR THE METHOD

(71) Applicant: Shiu Kum Lam, Hong Kong (HK)

(72) Inventor: Shiu Kum Lam, Hong Kong (HK)

(*) Notice: Subject to any disclaimer, the term of this patent is extended or adjusted under 35 U.S.C. 154(b) by 0 days.

(21) Appl. No.: 15/370,053

(22) Filed: Dec. 6, 2016

(65) Prior Publication Data
US 2018/0153534 A1   Jun. 7, 2018

(51) Int. Cl.
| | |
|---|---|
| *A61B 18/14* | (2006.01) |
| *A61K 49/00* | (2006.01) |
| *A61B 10/04* | (2006.01) |
| *A61M 11/00* | (2006.01) |
| *A61B 17/3205* | (2006.01) |
| *A61B 17/34* | (2006.01) |
| *A61B 17/12* | (2006.01) |
| *A61B 17/30* | (2006.01) |
| *A61B 17/00* | (2006.01) |
| *A61B 90/00* | (2016.01) |

(52) U.S. Cl.
CPC ............ *A61K 49/006* (2013.01); *A61B 10/04* (2013.01); *A61B 17/12013* (2013.01); *A61B 17/32056* (2013.01); *A61B 17/3478* (2013.01); *A61M 11/007* (2014.02); *A61B 2017/00269* (2013.01); *A61B 2017/00296* (2013.01); *A61B 2017/00566* (2013.01); *A61B 2017/12018* (2013.01); *A61B 2017/306* (2013.01); *A61B 2090/395* (2016.02); *A61B 2217/007* (2013.01)

(58) Field of Classification Search
CPC ... A61B 17/00234; A61B 10/04; A61B 17/12; A61B 17/122; A61B 17/221; A61B 17/30; A61B 17/32056; A61B 17/3478; A61B 2017/00269; A61B 2017/2215; A61B 2017/306; A61B 2217/005; A61B 2217/007; A61B 2018/141; A61M 11/007; A61K 49/006
See application file for complete search history.

(56) References Cited

U.S. PATENT DOCUMENTS

| | | | | |
|---|---|---|---|---|
| 5,651,788 | A * | 7/1997 | Fleischer | A61B 18/14 606/37 |
| 6,007,546 | A * | 12/1999 | Snow | A61B 18/10 606/110 |
| 6,319,260 | B1 | 11/2001 | Yamamoto | 606/113 |

(Continued)

OTHER PUBLICATIONS

Trivedi, P. J., and B. Braden. "Indications, stains and techniques in chromoendoscopy." The Quarterly Journal of Medicine, Oct. 24, 2012, pp. 117-131.*

(Continued)

*Primary Examiner* — Jaymi E Della
(74) *Attorney, Agent, or Firm* — Ostrolenk Faber LLP

(57) ABSTRACT

For Endoscopic Mucosal Resection (EMR), particularly for the esophagus and stomach, a kit includes two endoscopes that are used alternatingly to separate chromoendoscopy for staining of intestinal metaplastic mucosa, injecting solution to raise diseased mucosa, snare polypectomy, and wound clipping from cap-assisted suction and ligation of the mucosa, for making these procedures more focused and readily accomplished, with less likelihood of bleeding and perforation.

12 Claims, 2 Drawing Sheets

(56) References Cited

U.S. PATENT DOCUMENTS

| | | | |
|---|---|---|---|
| 6,994,705 B2 | 2/2006 | Nobis | 606/37 |
| 9,248,147 B2 | 2/2016 | Yang | |
| 2005/0165272 A1 | 7/2005 | Okada et al. | 600/114 |
| 2008/0125804 A1* | 5/2008 | Gostout | A61B 1/018 606/192 |
| 2009/0036733 A1* | 2/2009 | Wallace | A61B 18/04 600/104 |
| 2009/0247823 A1* | 10/2009 | Yamamoto | A61B 18/1492 600/108 |

OTHER PUBLICATIONS

Canto, M. I. "Staining in Gastrointestinal Endoscopy: The Basics." Endoscopy, Aug. 31, 1999, pp. 479-486.*

M. Tada et al., "Endoscopic Resection of Early Gastric Cancer," Endoscopy 1993; 25:445-50.

K. S-H. Liu et al., "*Helicobacter pylori* associated gastric intestinal metaplasia: Treatment and surveillance," World J Gastroenterol. 2016; 22(3):1311-1320.

J.H. Hwang, et al., "Endoscopic mucosal resection," Gastrointestinal Endoscopy 2015; 82(2):215-226.

H. Inoue et al., "Endoscopic mucosal resection with a cap-fitted panendoscope for esophagus, stomach, and colon mucosal lesions," Gastrointestinal Endoscopy 1993; 39:58-62.

First Examination Report dated Apr. 11, 2018 in corresponding Australian Patent Application No. 2017272212.

H. Inoue et al., "A new simplified technique of endoscopic esophageal mucosal resection using a cap-fitted panendoscope (EMRC)," Surg Endosc. 1992; 6:264-265.

Chapter 33 of Clinical Gastrointestinal Endoscopy, Second Edition, Ginsberg et al., 2005, 2012, entitled "Endoscopic Therapy for Gastric Neoplasms," Ryu et al., pp. 425-447.

* cited by examiner

TWO-ENDOSCOPE TECHNIQUE OF ENDOSCOPIC MUCOSAL RESECTION AND KIT WITH A SET OF ENDOSCOPES FOR THE METHOD

BACKGROUND OF THE INVENTION

Endoscopic mucosal resection (EMR) was pioneered in Japan for management of early gastric cancer (Tada M., Murakami A., Karita M. et al. Endoscopic resection of early gastric cancer. *Endoscopy* 1993; 25: 445-50.). This procedure has gained wider acceptance as a therapeutic option for various gastrointestinal lesions, including Barrett's esophagus (i.e. intestinal metaplasia of the esophagus, a precancerous pathology), and colorectal adenomas and early cancers. It can also be extended to treat intestinal metaplasia of the gastric antrum, which is also precancerous, and which often persists after treatment of *Helicobacter pylori* (*Helicobacter pylori* associated gastric intestinal metaplasia: Treatment and surveillance. Liu K S H, Wong I O L, Leung W K. World J Gastroenterol. 2016; 22(3): 1311-1320), a known cause of chronic gastritis, gastric intestinal metaplasia, and gastric cancer.

Chromoendoscopy using an appropriate staining dye, such as methylene blue, is used to identify the mucosa with intestinal metaplasia, a lesion. 0.5% methylene blue is sprayed through a cannula onto the mucosa at least around the area of a lesion. This is followed about two minutes later by vigorous washing of the mucosa. Mucosa with intestinal metaplasia remains persistently stained at the lesion despite the washing.

Typical existing techniques of endoscopic mucosal resection use a single standard endoscope with specially designed, commercially available endoscope caps. Examples of such techniques and of the endoscopes used to perform the techniques are described in "Endoscopic Mucosal Resection" by J. H. Hwang et al. in Vol. 82, No. 2:2015, Gastrointestinal Endoscopy, pp. 215-226, and in "Endoscopic Ultrasound and Endoscopic Ultrasound-Guided Fine Needle Aspiration Cytology," a portion of Chapter 33 of Clinical Gastrointestinal Endoscopy, Second Edition, Ginsberg et al., 2005, 2012, entitled "Endoscopic Therapy for Gastric Neoplasms," Ryu et al., on page 431, the immediately preceding printed publication source corresponding to the online source referenced in the originally filed specification.

Endoscopes with two biopsy channels, rather than one biopsy channel are known.

Endoscopes with two biopsy channels are generally not available in normal endoscope theaters because the need for such endoscopes is infrequent, their size is bulky, and their cost is high.

Cap-assisted EMR typically uses submucosal injection to lift the target lesion at the mucosa. Dedicated mucosectomy devices that use a cap affixed to the distal tip of the endoscope are available. The cap is usually equipped with a specially designed, crescent-shaped electrocautery snare that is opened and positioned on an internal circumferential ridge at the tip of the cap. The endoscope is then positioned immediately over the target lesion, suction is used to retract the mucosa into the cap, and the snare is closed to capture and resect the lesion. Because no ligation is used after the retraction and before the snare is closed, and because the resection area is broad-based, bleeding can be a complication.

Ligation-assisted EMR uses a banding cap attached to the distal open end of the endoscope and positions the cap over the target lesion with or without prior submucosal injection. Suction applied to the endoscope causes the lesion to be sucked into the cap. A band is deployed from a band ligator equipped with a band to ligate the lesion to form an artificial polyp. That polyp is then resected using a specially designed snare through the banding device.

If no submucosal injection is used, the suction on the lesion could include submucosa and the layers underneath, so that perforation can be a complication. If needle injection is used, the needle injection needs to be performed within the confined size of the cap and the needle is likely to be in a vertical orientation over the lesion, so that positioning the needle accurately in the submucosal layer is not readily accomplished, and good elevation of the mucosa may not be achieved, posing a danger to subsequent EMR.

OBJECTS OF THE INVENTION

An object of the invention is to provide a simple and safe endoscopic technique for endoscopic mucosal resection (EMR) of gastrointestinal mucosa affected with intestinal metaplasia or any lesion that can be resected by EMR.

It is another object of this invention to provide a method and apparatus to minimize the complication of bleeding and perforation during EMR and performance of the method is minimally invasive.

It is a further object to use standard endoscopes for EMR, rather than one endoscope specially adapted for EMR.

SUMMARY OF THE INVENTION

A two-endoscope technique of Endoscopic Mucosal Resection (EMR) is disclosed. A kit comprising two separate standard endoscopes, a first one uncapped at its distal end region toward the mucosa and the second one capped at its distal end region, are used alternately to perform different functions. The first uncapped endoscope is used for chromoendoscopy, injection, snaring, clipping of wound and recovery of specimens, and the second capped endoscope is used for suction and ligation. Such division of functions enables focusing and simplification of jobs, which avoids need for specialized endoscope constructions and enables use by an endoscopist not trained in using an endoscope specially adapted for performing an entire EMR process.

The first uncapped endoscope is used for snare polypectomy of the artificial polyp. Because endoscopists are familiar with snare polypectomy through an uncapped endoscope, as opposed to a capped endoscope, snare polypectomy of the artificial polyp can be achieved readily.

The first uncapped endoscope is used to perform chromoendoscopy with a staining dye for lesions, such as methylene blue, and needle injection of the mucosa at the lesion and into the submucosa that supports the mucosa with a liquid, such as normal saline solution, to lift the persistently stained mucosa that represents intestinal metaplasia or other lesion. This first uncapped endoscope is then withdrawn, and replaced with the second capped endoscope, the cap being a readily and commercially available cap used for ligation of esophageal varices and other lesions. The second capped endoscope focuses on applying suction of the elevated stained mucosa followed by deploying of a ligature to turn the mucosa into an artificial polyp. The cap used for ligation of esophageal varices has been available for decades and its use is familiar to many endoscopists. The cap for esophageal ligation is used instead of a specially designed cap for endoscopic mucosal resection. The method using a known cap on the endoscope is simple and can be achieved by endoscopists who are familiar with endoscopic ligation of esophageal varices.

The first endoscope is not capped, allowing clear and uncompromised view for procedures including chromoendoscopy, injection, snaring, clipping and specimen recovery to be executed accurately and readily.

A specially designed cap for EMR is not used. It can be envisaged that all the functions performed with such a cap on one endoscope may not be satisfactorily and readily accomplished within the confined space of such a cap. Furthermore, use of cap-assisted EMR would require training or familiarization, before it can be used with confidence.

The second endoscope is pre-fitted with a cap for ligation of esophageal varices and is focused on the functions of suction and ligation of the mucosa that is raised and persistently stained with methylene blue.

Because suction of the saline raised mucosa is used, organ perforation should not occur. Because ligation of the saline raised mucosa is used, bleeding should not occur on subsequent snare polypectomy of the artificial polyp.

After withdrawing the second endoscope, the first uncapped endoscope is re-passed to perform snare resection of the artificial polyp. Clips may be used to close the wound.

This method, unlike existing ones that employ a single endoscope having a specially designed and more expensive cap for EMR, provides clear endoscopic vision and allows endoscopic procedures that are not compromised by the confinement of the cap, and should thereby lessen complications of bleeding and perforation.

Because of use of two different endoscopes, uncapped and capped, the method can be performed by many endoscopists without need for special training or familiarization in using the specially designed cap for endoscopic mucosal resection.

The Two-Endoscope Technique of EMR uses two standard endoscopes. It may be used to treat Barrett's esophagus, i.e. intestinal metaplasia of the lower end of the esophagus, and gastric antral intestinal metaplasia and may be used to treat other lesions. The method using two endoscopes can be applied to EMR for early cancer, raised or flat adenomas, MALToma and similar lesions of the gastrointestinal tract. Because of the need to exchange endoscopes, it is recommended that it be used for pathological lesions located in the upper gastrointestinal tract and the distal colon.

The method using the two endoscopes for EMR is next described. It is followed by illustrations and descriptions of the steps performed using each type of endoscope and other elements of the kit described herein.

The Two-Endoscope Technique of EMR comprises: using the first (uncapped) endoscope to perform chromoendoscopy with 10% n-acetylcholine to remove mucus followed by using 5% methylene blue—as a staining dye to stain and thereby identify the area and extent of intestinal metaplasia; after a time period sufficient to stain a lesion on the mucosa, washing the mucosa to remove stain from around the lesion, but not remove stain from the lesion; lifting the stained mucosa with a submucosal injection (about 10 ml) of saline solution containing 1:100,000 adrenaline; withdrawing the first endoscope and inserting quickly, particularly before the lifted mucosa collapses due to diffusion/absorption of saline to/by the neighboring tissue, a second (capped) endoscope, on which a cap (with usually 5 rubber bands) used for ligation of esophageal varices has already been attached; sucking the raised mucosa into the cap; ligating the lesion on the raised mucosa to transform it into an artificial polyp; performing more ligations and creating more artificial polyps if needed; withdrawing the second endoscope and re-inserting the first uncapped endoscope; resecting the artificial polyp(s) with an ordinary snare; retrieving the resected specimens with a basket; applying clips to close the wound(s) considered large (e.g. over 15 mm) to allow quicker healing.

Illustrations of the steps described above are shown in the Figures and are described in the following text.

DESCRIPTION OF AN EMBODIMENT

A kit including a set of endoscopes and other elements used in or with the endoscopes performs the method.

Figure 1:
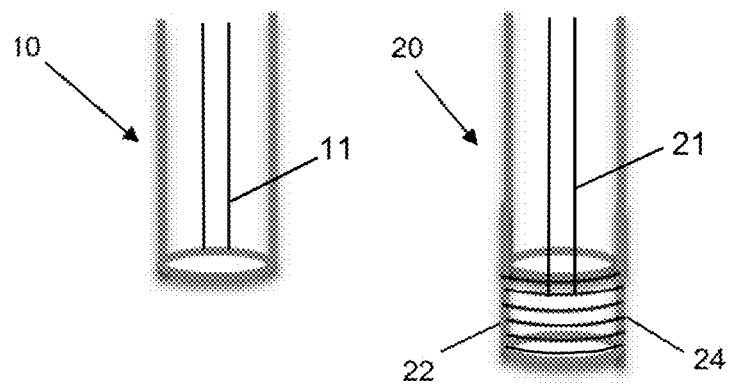
FIG. 1 shows the leading or distal ends of two endoscopes to perform the method hereof.

FIG. 1 shows the leading or distal ends of two standard or conventional endoscopes 10 and 20 ready to perform the method hereof. Each endoscope has a respective biopsy channel 11, 21 from its distal end. As conventional endoscopes have known features, their relevant construction features are illustrated schematically.

The first endoscope 10 is a normal uncapped endoscope such as an esohpago-gastro-duodenoscope offered by Olympus (model 290). The second endoscope 20 of the same type and supplies is capped with an attached cap 22 used for ligation of esophageal varices, such as MBL-6 (Six Shooter Saeed Multi-band Ligator), offered by Cook Medical and containing six rubber ligation bands 24.

Figure 2:
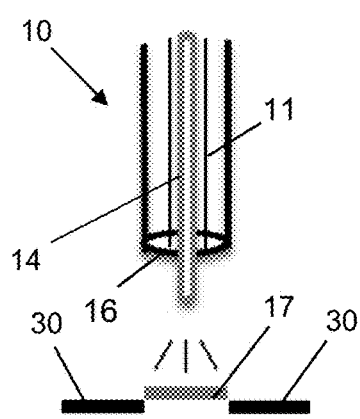
FIG. 2 shows the first endoscope with a spray cannula for a mucosa staining agent.

In FIG. 2, the first endoscope 10 is passed with its open distal end 16 toward a mucosa 30 with a possible lesion 17. A spray cannula 14 passing through the biopsy channel of the first endoscope is used to spray the mucosa of the lower end of the esophagus for Barrett's esophagus or of the antrum, body and fundus of the stomach for intestinal metaplasia. The spray cannula 14 first sprays the mucosa with 10% n-acetylene choline to remove mucus, and then sprays the mucosa with a staining dye 5% solution of methylene blue. After two minutes, sufficient for the staining dye to stain the lesion, the mucosa 30 is vigorously washed with water to remove stain except on the lesion. A persistently stained area of the mucosa at 17 represents a lesion, such as intestinal metaplasia.

Figure 3:
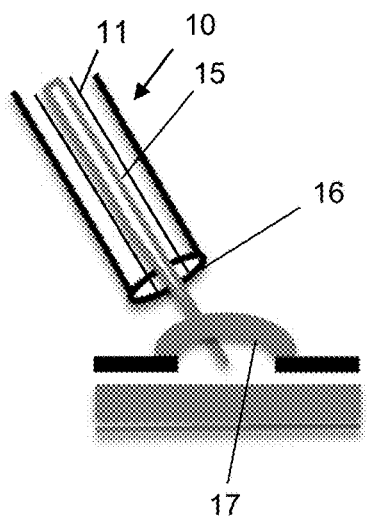
FIG. 3 shows the first endoscope with a needle for injection of normal saline solution and the resultant elevated mucosa.

In FIG. 3, a needle 15 is inserted through the biopsy channel of the first endoscope and past the distal end 16 of the first endoscope 10 and through a persistently stained mucosa 17 into the submucosa that supports the mucosa. Then about 10 ml of normal saline solution is injected to elevate the mucosa 17, as seen in FIG. 3. It is recommended that not more than two stained areas 17 should undergo injection elevation at any one time, since the elevation will collapse over time due to diffusion/absorption of saline to/by the surrounding tissue. The first endoscope is then withdrawn.

Figure 4:
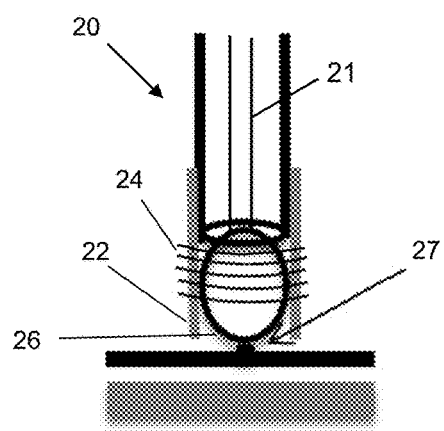
FIG. 4 shows the leading or distal end of the second capped endoscope and shows a polyp formed by the second endoscope.

In FIG. 4, the open distal end of the second capped endoscope 20, pre-fitted with a variceal ligation cap 22, is immediately passed to the stained mucosa 17. The stained mucosa 17 is then sucked into the cap 22, together with the saline solution inside the mucosa. The suction is applied in the biopsy channel of the second endoscope 20 and at the cap 22. The second endoscope is inserted quickly to reach the raised mucosa 17 before the injected solution diffuses away to, or is absorbed by, the surrounding tissue.

Then a ligation band 24 is deployed from the cap to ligate the base region 27 of the sucked up stained mucosa, resulting in the mucosa forming an artificial saline containing polyp 26 in the cap 22. If another mucosal elevation has been performed, this procedure can be repeated to form another artificial polyp. The capped endoscope 20 is then withdrawn.

Figure 5:
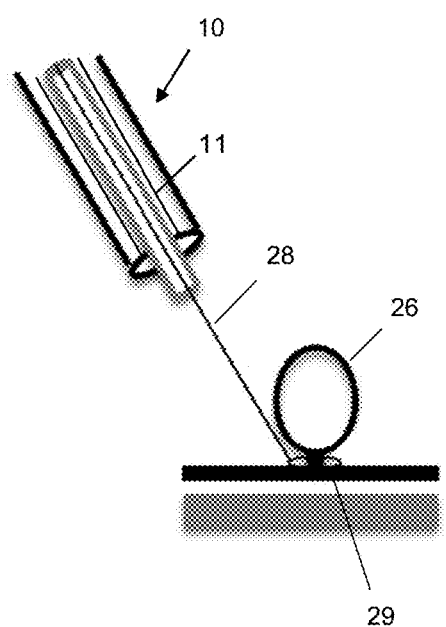
FIG. 5 shows the snaring of the polyp for resection.

In FIG. 5, the first uncapped endoscope is again passed with its distal end toward the mucosa, and a snare 28, 29 is positioned to and is used to resect the artificial polyp 26, which is subsequently retrieved with a basket (not shown) for histological examination. The snare is shown in a position to resect an artificial polyp 26 created by the ligation.

The present invention is not limited to the embodiments described above. Various alternatives, modifications and equivalents can be used. For this reason, the embodiments named above do not limit the scope of the invention, which is defined by the attached patent claims.

What is claimed is:

1. A method for endoscopic mucosal resection (EMR) using a kit comprising a first and a second endoscope, the method comprising:
    moving the first endoscope with an open distal end and a first biopsy channel toward a mucosa in a region of a lesion;
    deploying a spray cannula through the first biopsy channel of the first endoscope;
    performing chromoendoscopy by spraying, through the spray cannula, a liquid staining dye on a mucosa around the lesion and on a mucosa of the lesion to stain the lesion;
    washing the mucosa in the region of the lesion to remove a stain of the liquid staining dye from the mucosa around the lesion, while a persistently stained area of the mucosa of the lesion remains after the washing of the mucosa in the region of the lesion;
    passing an injection needle through the first biopsy channel of the first endoscope, inserting the injection needle through the persistently stained area of the mucosa of the lesion into a submucosa, which supports the mucosa of the lesion, and injecting a liquid, by the injection needle, into the submucosa to elevate the persistently stained area of the mucosa of the lesion in a region of the injection of the liquid to form an elevated mucosa of the lesion;
    then withdrawing the first endoscope;
    moving the second endoscope, which has a second biopsy channel and is pre-fitted with an end cap at a distal end of the second endoscope, toward the persistently stained area of the mucosa of the lesion;
    sucking, by the second biopsy channel of the second endoscope and by the end cap, the persistently stained area of the mucosa of the lesion along with the injected liquid into the end cap of the second endoscope and applying sufficient suction on the persistently stained area of the mucosa of the lesion to draw the persistently stained area of the mucosa of the lesion into the end cap;
    deploying a ligature from the end cap to ligate the persistently stained area of the mucosa of the lesion, the ligated persistently stained area of the mucosa of the lesion forming an artificial polyp while the artificial polyp is attached to the mucosa around the lesion;
    then withdrawing the second endoscope and leaving the artificial polyp attached to the mucosa around the lesion;
    moving the open distal end of the first endoscope toward the artificial polyp, and, by use of a snare through the first biopsy channel of the first endoscope, resecting the artificial polyp from the mucosa around the lesion;
    wherein both of the first and the second endoscopes contribute to the endoscopic mucosal resection and the first biopsy channel of the first endoscope is an only channel of the first endoscope configured to permit passage of an instrument through the first endoscope.

2. The method of claim 1, further comprising retrieving the resected artificial polyp by use of a basket after the resecting.

3. The method of claim 1, wherein the injected liquid is a normal saline solution.

4. The method of claim 1, further comprising removing the first endoscope from the region of the persistently stained area of the mucosa of the lesion after the injection of the liquid and prior to a collapse of the elevated mucosa; and
    immediately moving the distal end of the second endoscope and the end cap of the second endoscope to the persistently stained area of the mucosa of the lesion prior to the sucking of the persistently stained area of the mucosa of the lesion into the end cap and before the collapse of the elevated mucosa.

5. The method of claim 1, further comprising producing more than one of the elevated mucosa of the lesion with the injection needle applied to more than one of the region of injection of the liquid, and removing the first endoscope from persistently stained areas of the mucosa of more than one lesion to prevent a collapse of elevations of injected mucosa.

6. The method of claim 1, further comprising before spraying the liquid staining dye on the mucosa around the lesion and on the mucosa of the lesion, spraying the mucosa around the lesion and on the mucosa of the lesion through the spray cannula with a liquid for removing mucus from the mucosa around the lesion and on the mucosa of the lesion.

7. The method of claim 6, wherein the liquid for removing mucus is 10% n-acetylene choline.

8. The method of claim 1, further comprising after the resecting, applying clips to a wound in the mucosa around the lesion caused by the resecting.

9. The method of claim 1, wherein the washing of the mucosa after the spraying of the liquid staining dye on the mucosa is with a liquid and at a flow rate to remove the stain of the liquid staining dye from the mucosa around the lesion, but not to remove the stain of the liquid staining dye from the persistently stained area of the mucosa of the lesion.

10. The method of claim 1, further comprising, following the resecting of the artificial polyp, retrieving the resected artificial polyp from the mucosa around the lesion to which the artificial polyp was attached.

11. The method of claim 1, wherein, after a period of time sufficient for the liquid staining dye to stain the mucosa of the lesion, performing the washing of the mucosa in the region of the lesion.

12. The method of claim 1, wherein the liquid staining dye sprayed comprises 5% methylene blue.

* * * * *